US00PP34894P2

(12) United States Plant Patent
Post

(10) Patent No.: US PP34,894 P2
(45) Date of Patent: Jan. 3, 2023

(54) ***CHRYSANTHEMUM* PLANT NAMED 'DLFDORO3'**

(50) Latin Name: ***Chrysanthemum* X *morifolium***
Varietal Denomination: 'DLFDORO3'

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/833,762

(22) Filed: Jun. 6, 2022

Related U.S. Application Data

(60) Provisional application No. 63/197,948, filed on Jun. 7, 2021.

(51) Int. Cl.
*A01H 5/02* (2018.01)
*A01H 6/14* (2018.01)

(52) U.S. Cl.
USPC ..... Plt./291
CPC ..... *A01H 6/1424* (2018.05); *A01H 5/02* (2013.01)

(58) Field of Classification Search
USPC ..... Plt./263.1, 284, 286, 287, 291
See application file for complete search history.

(56) References Cited

U.S. PATENT DOCUMENTS

PP20,391 P2 * 10/2009 Pieters ..... A01H 5/02
Plt./291

* cited by examiner

*Primary Examiner* — Karen M Redden
(74) *Attorney, Agent, or Firm* — C. Anne Whealy

(57) ABSTRACT

A new and distinct cultivar of *Chrysanthemum* plant named 'DLFDORO3', characterized by its upright plant habit; uniform growth habit; vigorous growth habit and rapid growth rate; durable and robust dark green-colored leaves; strong upright flowering stems; decorative-type inflorescences with light pink-colored ray florets; and good post-production longevity.

2 Drawing Sheets

Figure 1:
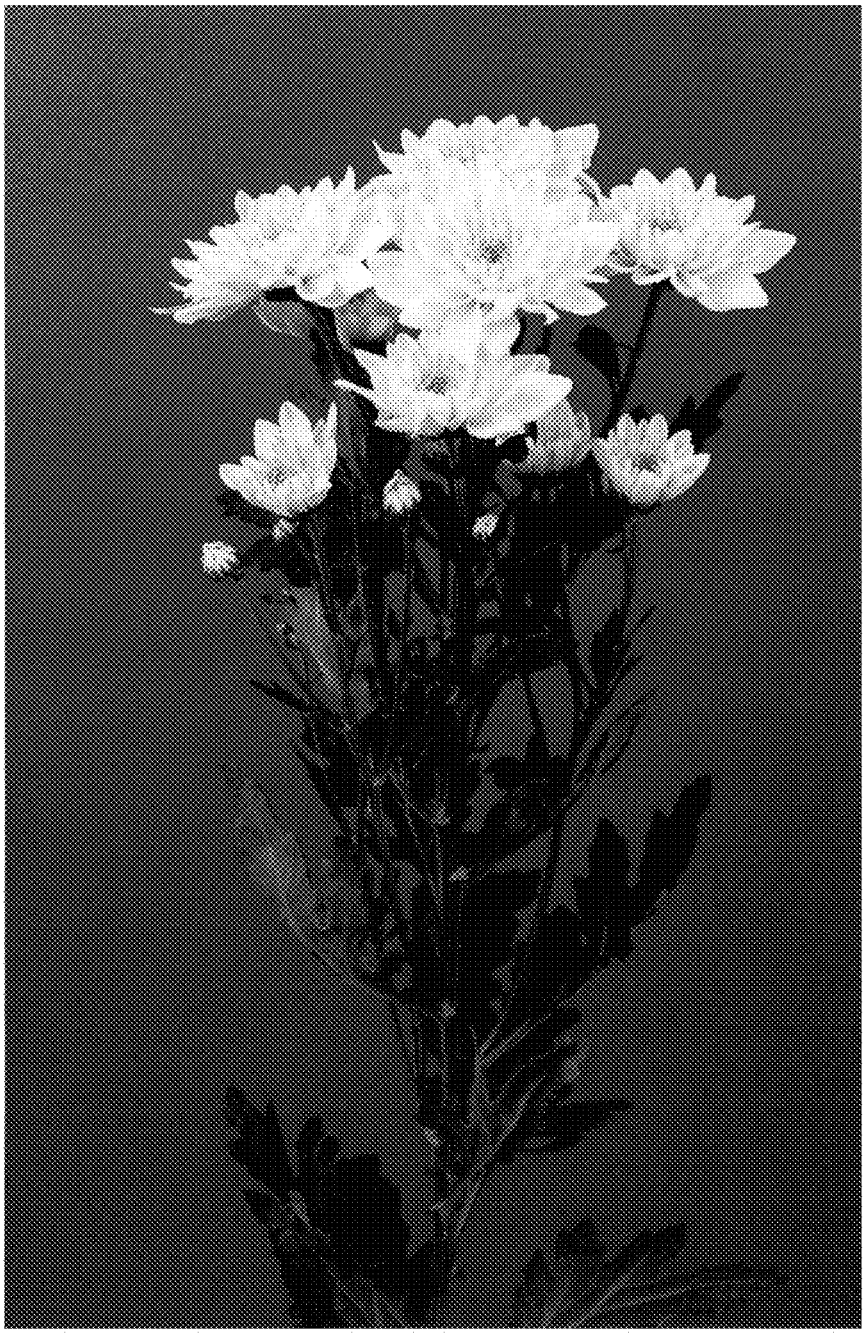

Botanical designation: *Chrysanthemum* X *morifolium*.
Cultivar denomination: 'DLFDORO3'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFDORO3'.

The new *Chrysanthemum* plant is a product of a planned breeding program conducted by the Inventor in Maasdijk, The Netherlands. The objective of the breeding program is to create new cut flower *Chrysanthemum* plants with unique and attractive inflorescences.

The new *Chrysanthemum* plant originated from a cross-pollination in August, 2017 of a proprietary selection of *Chrysanthemum* x *morifolium* identified as code number KR 10354, not patented, as the female, or seed, parent with a proprietary selection of *Chrysanthemum* x *morifolium* identified as code number KR 2011.0184-3, not patented, as the male, or pollen, parent. The new *Chrysanthemum* plant was discovered and selected as a single flowering plant from within the progeny of the stated cross-pollination in a controlled greenhouse environment in Maasdijk, The Netherlands in April, 2018.

Asexual reproduction of the new *Chrysanthemum* plant by vegetative terminal cuttings in a controlled greenhouse environment in Maasdijk, The Netherlands since April, 2018 has shown that the unique features of this new *Chrysanthemum* plant are stable and reproduced true to type in successive generations of asexual reproduction.

SUMMARY OF THE INVENTION

The following traits have been repeatedly observed and are determined to be the unique characteristics of 'DLFDORO3'. These characteristics in combination distinguish 'DLFDORO3' as a new and distinct *Chrysanthemum* plant:

1. Upright plant habit; uniform growth habit.
2. Vigorous growth habit and rapid growth rate.
3. Durable and robust dark green-colored leaves.
4. Strong upright flowering stems.

5. Decorative-type inflorescences with light pink-colored ray florets.
6. Good postproduction longevity.

Plants of the new *Chrysanthemum* differ primarily from plants of the female parent selection in the following characteristics:

1. Ray florets of plants of the new *Chrysanthemum* are not as carinate as ray florets of plants of the female parent selection.
2. Ray florets of plants of the new *Chrysanthemum* are lighter pink in color than ray florets of plants of the female parent selection.

Plants of the new *Chrysanthemum* differ primarily from plants of the male parent selection in the following characteristics:

1. Leaf sinuses of plants of the new *Chrysanthemum* are more convergent than leaf sinuses of plants of the male parent selection.
2. Ray floret apices of plants of the new *Chrysanthemum* are bluntly acute with occasional shallow indentations whereas ray floret apices of plants of the male parent selection are praemorse.

Plants of the new *Chrysanthemum* can be compared to plants of *Chrysanthemum* X *morifolium* 'DLFROC3', not patented. In side-by-side comparisons, plants of the new *Chrysanthemum* differ primarily from plants of 'DLFROC3' in the following characteristics:

1. Leaf sinuses of plants of the new *Chrysanthemum* are more convergent than leaf sinuses of plants of 'DLFROC3'.
2. Ray floret apices of plants of the new *Chrysanthemum* are bluntly acute with occasional shallow indentations whereas ray floret apices of plants of 'DLFROC3' are emarginate.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) is a side perspective view of a typical flowering stem of 'DLFDORO3' grown as a spray-type cut flower.

Figure 2:
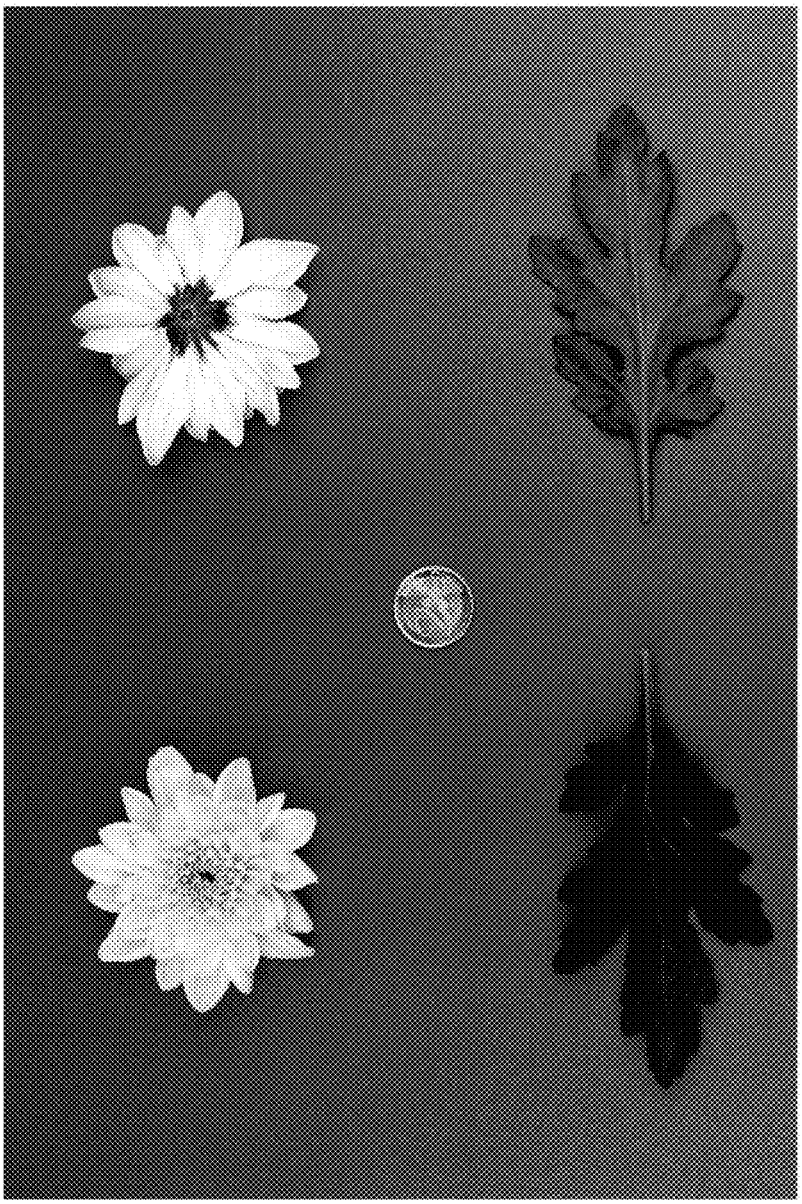

The photograph on the second sheet (FIG. 2) is a close-up view of upper (left) and lower (right) surfaces of typical inflorescences and typical leaves of 'DLFDORO3'.

DETAILED BOTANICAL DESCRIPTION

The aforementioned photographs and following observations and measurements describe plants grown during the spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 7 klux. Plants were grown as single-stem spray-type plants and were ten weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFDORO3'.

Parentage:

*Female, or seed, parent*.—Proprietary selection of *Chrysanthemum* x *morifolium* identified as code number KR 10354, not patented.

*Male, or pollen, parent*.—Proprietary selection of *Chrysanthemum* x *morifolium* identified as code number KR 2011.0184-3, not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem spray-type; upright plant habit; vigorous growth habit and rapid growth rate.

*Plant height, soil level to top of foliar plane*.—About 74.3 cm.

*Plant height, soil level to top of inflorescence plane*.—About 83.1 cm.

*Plant (spray) diameter*.—About 20.3 cm.

*Flowering stem length*.—About 71.1 cm.

*Flowering stem diameter*.—About 7 mm.

*Flowering stem internode length*.—About 2.6 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 144A.

*Flowering stem color, developed*.—Close to 144A; at the ridges, close to 147D.

*Leaf description*.—Arrangement: Alternate; simple. Length: About 11.1 cm. Width: About 7.5 cm. Shape, in overall outline: Elliptic to broadly oblong. Apex: Abruptly acute. Base: Attenuate. Margin: Palmately lobed, coarsely dentate to serrate; sinuses convergent and medium to deep in depth; not undulate. Texture and luster, upper surface: Moderately to densely pubescent, not rugose; slightly velvety; matte to slightly glossy. Texture and luster, lower surface: Moderately pubescent, not rugose; slightly velvety; matte. Venation pattern: Pinnate. Color: Developing leaves, upper surface: Close to 137B. Developing leaves, lower surface: Close to 138B. Fully developed leaves, upper surface: Slightly darker than 137A; venation, close to 146C. Fully developed leaves, lower surface: Close to 147B; venation, close to 146D. Petioles: Length: About 2.8 cm. Diameter: About 3 mm by 3 mm. Strength: Moderately strong. Texture and luster, upper surface: Densely pubescent; moderately glossy. Texture and luster, lower surface: Densely pubescent; slightly glossy. Color, upper surface: Close to 146C; edges, close to 143A. Color, lower surface: Close to 146D; edges, close to 147B. Stipules: Quantity and appearance: Two leafy stipules, opposite, at the petiole attachment to the stem. Length: About 7 mm. Width: About 1 cm. Shape: Reniform; apex, acute to short apiculate; base, broadly cuneate; margins, entire. Texture and luster, upper surface: Moderately to densely pubescent; matte to slightly glossy. Texture and luster, lower surface: Moderately pubescent; matte. Color, upper surface: Darker than 137A. Color, lower surface: Close to 147B.

Inflorescence description:

*Appearance*.—Decorative-type inflorescence form with obovate to oblanceolate-shaped ray florets and tubular disc florets; inflorescences, rotate and flattened in overall shape; inflorescences borne perpendicular to peduncles and face upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 52 days later when grown as a spray-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a spray-type, about 15 inflorescences (varying between 10 and 21) develop per flowering stem.

*Inflorescence size*.—Diameter: About 8.8 cm. Depth (height): About 2.6 cm. Disc diameter: About 4 mm; inconspicuous.

*Receptacles*.—Height: About 4 mm. Diameter: About 6 mm. Shape: Broadly ovate. Color: Close to 145C.

*Inflorescence buds*.—Height: About 1.2 cm. Diameter: About 1.4 cm. Shape: Flattened spherical. Texture and luster: Sparsely to moderately pubescent; slightly glossy. Color: Developing involucral bracts, close to 137C and 145B; developing ray florets, close to a blend of 76C and 76D.

*Ray florets*.—Quantity and arrangement: About 240 arranged in about six whorls. Length: About 2.8 cm, varying between 0.5 cm and 4.2 cm. Width: About 1 cm, varying between 0.1 cm and 1.5 cm. Shape: Obovate to oblanceolate; slightly to moderately concave; moderately carinate. Apex: Bluntly acute to shallowly emarginate. Base: Cuneate. Margin: Entire; not undulate. Aspect: About 45° from vertical, varying from 20° to 70° from vertical. Texture and luster, upper and lower surfaces: Smooth, glabrous; slightly velvety; matte. Color: When opening, upper and lower surfaces: Close to 75C to 75D. Fully opened, upper surface: Close to NN155D slightly tinged with close to 75D; towards the base, close to 69D; venation, similar to lamina colors; color does not change with subsequent development. Fully opened, lower surface: Close to a blend of N155B and NN155D; venation, similar to lamina colors; color does not change with subsequent development.

*Disc florets*.—Quantity and arrangement: About 80 randomly arranged at the center of the receptacle; disc florets typically do not fully develop. Length: About 3 mm. Diameter: About 0.8 mm. Shape: Tubular. Apex: Obtuse. Margin, free-part: Entire. Texture and luster, inner and outer surfaces: Smooth, glabrous; glossy. Color, when opening and fully opened: Towards the apex, close to 151B; mid-section and towards the base, close to 145C.

*Involucral bracts*.—Quantity and arrangement: About 24 arranged in about three whorls. Length: About 1 cm. Width: About 3.5 mm. Shape: Oblong to ovate. Apex: Bluntly acute. Base: Cuneate. Margin: Entire. Texture and luster, upper surface: Smooth, glabrous; glossy. Texture and luster, lower surface: Sparsely pubescent; matte. Color, upper surface: Close to 143A; lateral margins, translucent and close to 196D and apical margins tinged with close to N199A. Color, lower surface: Close to 146A to 146B; lateral margins, translucent and close to 196D and apical margins tinged with close to N199A.

*Peduncles*.—Length: About 7.3 cm. Diameter: About 4 mm. Strength: Strong. Aspect: Upright. Texture and luster: Moderately pubescent; moderately glossy. Color: Close to 143A; at the ridges, close to 145A to 145B.

*Reproductive organs*.—Androecium: To date, stamen development has not been observed on plants of the new *Chrysanthemum*. Gynoecium: Present only on ray florets as disc florets do not fully develop. Quantity: One per floret. Pistil length: About 6 mm. Style length: About 5 mm. Style color: Close to 150D. Stigma diameter: About 0.75 mm. Stigma shape: Cleft, decurrent. Stigma color: Close to 14A to 14B. Ovary color: Close to 157A.

*Seeds and fruits*.—To date, seed and fruit development have not been observed on plants of the new *Chrysanthemum*.

Pathogen & pest resistance: Plants of the new *Chrysanthemum* have been observed to be resistant to Western Flower Thrips (*Frankliniella occidentalis*). To date, plants of the new *Chrysanthemum* have not been observed to be resistant to pathogens and other pests common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFDORO3' as illustrated and described.

* * * * *